United States Patent
Spector

(10) Patent No.: US 11,419,770 B2
(45) Date of Patent: Aug. 23, 2022

(54) BANDAGE WITH UV DISINFECTANT AND MICRONEEDLES FOR ANTIMICROBIAL DELIVERY AND FLUID ABSORPTION FROM A WOUND

(71) Applicant: NYMC Biotechnology Commercialization, LLC, Valhalla, NY (US)

(72) Inventor: Donald Spector, Jupiter, FL (US)

(73) Assignee: NYMC BIOTECHNOLOGY COMMERCIALIZATION, LLC, Valhalla, NY (US)

( * ) Notice: Subject to any disclaimer, the term of this patent is extended or adjusted under 35 U.S.C. 154(b) by 49 days.

(21) Appl. No.: 16/887,429

(22) Filed: May 29, 2020

(65) Prior Publication Data

US 2020/0289330 A1    Sep. 17, 2020

Related U.S. Application Data

(63) Continuation-in-part of application No. 15/873,162, filed on Jan. 17, 2018, now Pat. No. 10,709,883, (Continued)

(51) Int. Cl.
| | |
|---|---|
| *A61F 13/02* | (2006.01) |
| *A61L 2/10* | (2006.01) |
| *A61N 5/06* | (2006.01) |
| *A61M 37/00* | (2006.01) |
| *A61F 13/00* | (2006.01) |

(52) U.S. Cl.
CPC .... *A61F 13/0206* (2013.01); *A61F 13/00063* (2013.01); *A61M 37/0015* (2013.01); *A61N 5/0624* (2013.01); *A61M 2037/0023* (2013.01); *A61M 2205/053* (2013.01); *A61N 2005/0645* (2013.01); *A61N 2005/0652* (2013.01); *A61N 2005/0661* (2013.01)

(58) Field of Classification Search
CPC ............... A61F 13/00063; A61L 15/44; A61L 2300/404; A61L 2300/062; A61L 2/10; A61M 37/0015; A61M 2037/0023; A61M 2037/003; A61M 2205/0205; A61M 2205/502; A61M 2205/8206; H02J 50/00; H02J 50/001; H02J 5/005; H02J 7/025; A61N 5/0624; A61N 5/0625; A61N 5/0616; A61N 2005/0651; A61N 2005/0661
See application file for complete search history.

(56) References Cited

U.S. PATENT DOCUMENTS

| | | |
|---|---|---|
| 3,504,064 A | 3/1970 | Bauer |
| 4,131,114 A | 12/1978 | Kirkpatrick et al. |
| (Continued) | | |

*Primary Examiner* — Camtu T Nguyen
(74) *Attorney, Agent, or Firm* — Collard & Roe, P.C.

(57) ABSTRACT

A bandage is formed of a film layer, an adhesive applied to the film layer, and an absorbent layer connected to the film layer. The absorbent layer comprises a compressed fabric soaked in a fluid. A permeable membrane is disposed over the absorbent layer and creates an electrical charge when fluid from the absorbent layer passes through the membrane. The electricity generated by the osmosis flows to a plurality of light emitting diodes that are connected to the membrane through a battery. The LEDs emit UV light to disinfect a wound when a bandage is applied to the wound.

8 Claims, 4 Drawing Sheets

Related U.S. Application Data which is a continuation-in-part of application No. 14/693,049, filed on Apr. 22, 2015, now abandoned, which is a continuation-in-part of application No. 13/795,055, filed on Mar. 12, 2013, now abandoned, which is a continuation-in-part of application No. 12/752,568, filed on Apr. 1, 2010, now Pat. No. 8,419,668.

(60) Provisional application No. 63/011,345, filed on Apr. 17, 2020, provisional application No. 62/573,042, filed on Oct. 16, 2017, provisional application No. 62/128,474, filed on Mar. 4, 2015, provisional application No. 61/310,332, filed on Mar. 4, 2010.

(56) References Cited

U.S. PATENT DOCUMENTS

| | | | |
|---|---|---|---|
| 4,241,007 A | 12/1980 | Tanaka et al. | |
| 4,273,115 A | 6/1981 | Holland et al. | |
| 4,376,438 A | 3/1983 | Straube et al. | |
| 4,411,262 A | 10/1983 | Von Bonin et al. | |
| 4,433,680 A | 2/1984 | Yoon | |
| 4,454,873 A | 6/1984 | Laufenberg et al. | |
| 4,502,479 A | 3/1985 | Garwood et al. | |
| 4,841,958 A | 6/1989 | Ersfeld et al. | |
| 4,984,566 A | 1/1991 | Sekine et al. | |
| 5,005,566 A | 4/1991 | Klintworth, Jr. | |
| 5,172,629 A | 12/1992 | Merry | |
| 5,277,954 A | 1/1994 | Carpenter et al. | |
| 5,370,927 A | 12/1994 | Scholz et al. | |
| 5,449,550 A | 9/1995 | Yasis et al. | |
| 5,474,522 A | 12/1995 | Scholz et al. | |
| 5,807,292 A | 9/1998 | Delmore | |
| 5,823,983 A | 10/1998 | Rosofsky et al. | |
| 5,997,492 A | 12/1999 | Delmore et al. | |
| 6,063,980 A | 5/2000 | Peterson et al. | |
| 6,077,240 A | 6/2000 | Sholz et al. | |
| 6,730,113 B2 | 5/2004 | Eckhardt et al. | |
| 6,967,261 B1 | 11/2005 | Soerens et al. | |
| 8,026,407 B2 | 9/2011 | Downs et al. | |
| 8,333,743 B2 | 12/2012 | Toreki et al. | |
| 2005/0148996 A1* | 7/2005 | Sun | A61Q 19/08 604/501 |
| 2007/0073201 A1 | 3/2007 | Campagna et al. | |
| 2011/0092871 A1 | 4/2011 | Fabo et al. | |
| 2011/0311610 A1 | 12/2011 | Mathies | |
| 2014/0048436 A1 | 2/2014 | Spector | |
| 2015/0238774 A1* | 8/2015 | Anderson | A61K 35/04 604/20 |
| 2016/0114186 A1* | 4/2016 | Dobrinsky | A61N 5/0624 607/94 |
| 2018/0043043 A1* | 2/2018 | Spector | A61F 13/00063 |

* cited by examiner

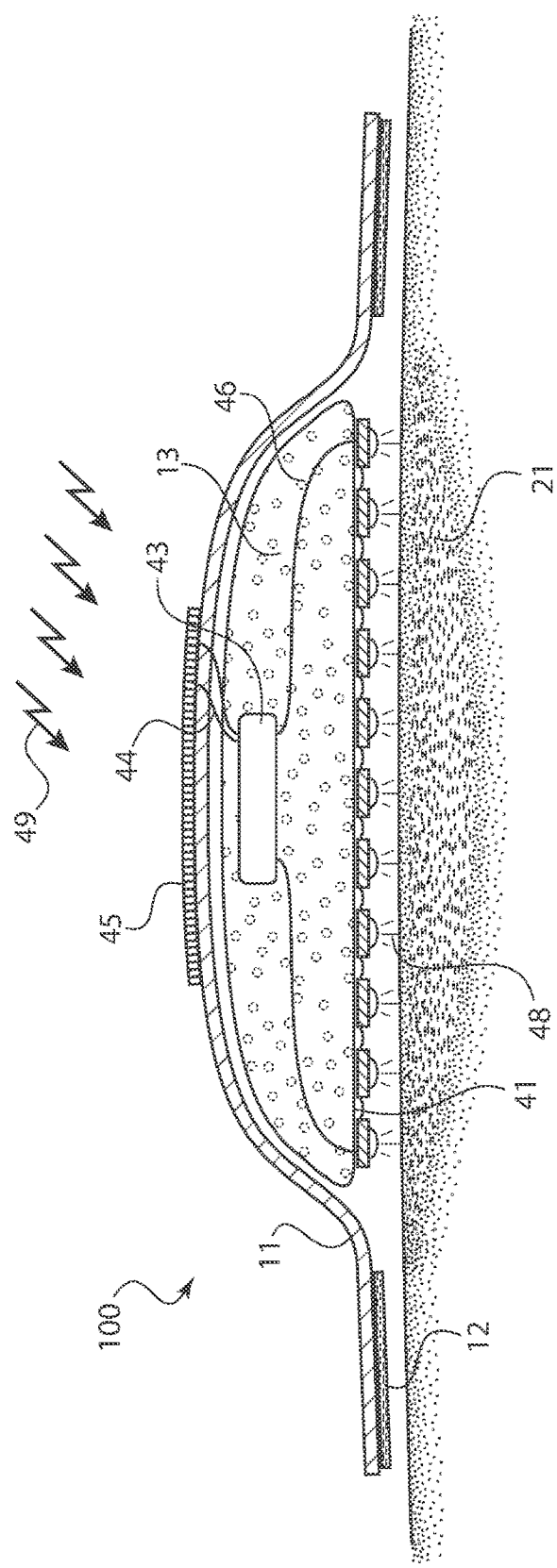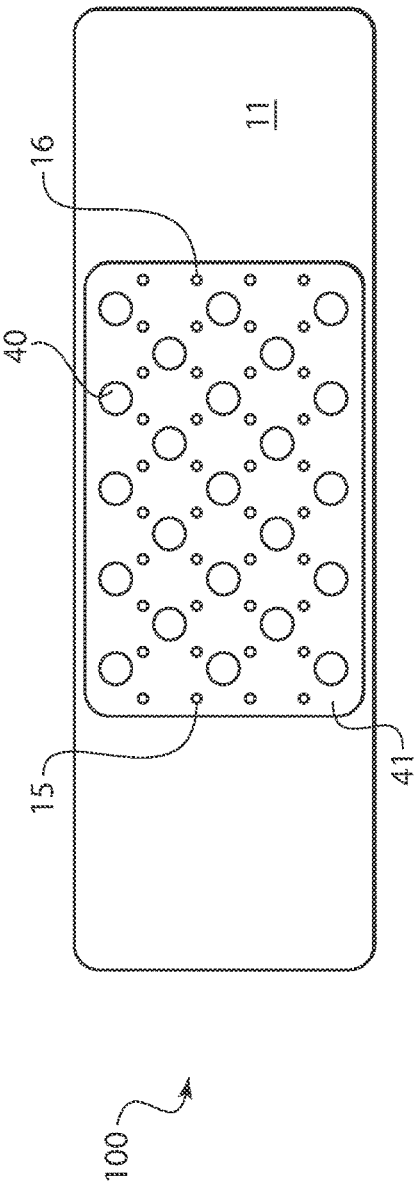

BANDAGE WITH UV DISINFECTANT AND MICRONEEDLES FOR ANTIMICROBIAL DELIVERY AND FLUID ABSORPTION FROM A WOUND

CROSS-REFERENCE TO RELATED APPLICATIONS

This Application claims priority under 35 USC 119(e) of U.S. Provisional Application No. 63/011,345, filed on Apr. 17, 2020. This application is also a continuation-in-part of U.S. patent application Ser. No. 15/873,162, filed on Jan. 17, 2018, which claims priority from U.S. Provisional Application No. 62/573,042 filed on Oct. 16, 2017, and which is a continuation-in-part of U.S. patent application Ser. No. 14/693,049, now abandoned, which claims priority under 35 USC 119(e) of U.S. Provisional Application Ser. No. 62/128,474, filed on Mar. 4, 2015 and which application is also a continuation-in-part of U.S. patent application Ser. No. 13/795,055, filed on Mar. 12, 2013, now abandoned, which is a continuation-in-part of U.S. patent application Ser. No. 12/752,568, filed on Apr. 1, 2010 (now U.S. Pat. No. 8,419,668 issued Apr. 16, 2013), which claims priority under 35 USC 119(e) of U.S. Provisional Application Ser. No. 61/310,332, filed on Mar. 4, 2010. The disclosures of all of these prior applications are herein incorporated by reference.

BACKGROUND OF THE INVENTION

1. Field of the Invention

The present invention relates to a bandage having a layer of absorbent material. In particular, the invention relates to a bandage having a layer of containing a plurality of microneedles that are adapted to suction fluid from a wound and also to inject antimicrobial agents in to the wound, as well as a source of UV light for disinfecting the wound.

2. The Prior Art

Present bandage strips typically consist of a layer of gauze padding connected to a longer strip of adhesive film or fabric. The gauze padding typically has a non-stick layer on its side facing the wound to keep the gauze from sticking to the wound. In addition, some bandages are treated with antimicrobial agents to prevent infection of the wound. For example, U.S. Pat. No. 6,967,261 to Soerens et al. discloses a bandage having a multilayer system connected to an adhesive strip. An antimicrobial agent is supplied to the bandage such that the agent can contact the wound.

While this type of bandage may be useful, some wounds are deep and/or large enough that the antimicrobial agent is insufficient for treating the entire wound. The bodily fluids collect in the wound and can cause infection.

UV light is sometimes used for disinfection purposes. U.S. Pat. No. 6,730,113 discloses having a UV catheter within a bandage for sterilizing or disinfecting a wound. The catheter is connected to a power source and a circuit board for controlling the light. While this may be an effective way to treat a wound with UV light, the equipment needed to power the light source is cumbersome and expensive.

SUMMARY OF THE INVENTION

It is therefore an object of the invention to provide a bandage having an antimicrobial agent and which also draws fluid away from the wound to speed healing and allow the agent to reach all areas of the wound. It is another object of the invention provide a source of UV light that acts to disinfect the wound. It is another object of the invention to provide the source of UV light such that the light is powered by osmosis from the fluid in the wound.

This object is accomplished by a bandage comprising a film layer having a top surface and a bottom surface, an adhesive applied to the bottom surface, and an absorbent layer connected to the bottom surface. The absorbent layer comprises an absorbent material that is also equipped with a plurality of microneedles that either absorb fluid from the wound, or are filled with antimicrobial agent, which is released into the wound. The needles act as conduits both into and out of the wound, so that over time, fluid collecting in the wound area is continually suctioned away and treated, thus decreasing healing time and risk of infection. The needles that absorb the fluid from the wound are attached directly to the absorbent material, and capillary action forces the fluid from the wound up the needles, where it is absorbed by the absorbent layer. At the same time, the other needles are either filled with the antimicrobial agent, or are connected to a reservoir of the agent, and the same capillary action that pulls the fluid out of the wound forces the agent, which is in liquid form, down the needles and into the wound.

In addition, due to the principle of chemotaxis, any organisms affected by the microbial agent will be driven up the microneedles to the absorbent layer, in order to avoid contact with the antimicrobial agent.

In a preferred embodiment, the antimicrobial agent is in communication with approximately half of the microneedles, with the other half being used to absorb the fluid from the wound.

In order to keep the antimicrobial agent from exiting the microneedles prior to use, a cover layer is placed over the absorbent layer and ends of the microneedles. The cover layer is removed immediately prior to use, which then allows the antimicrobial agent to flow through the microneedles and into the wound.

Any suitable antimicrobial agent can be used in the bandage according to the invention. In one embodiment, the antimicrobial agent is pre-loaded into the microneedles. The antimicrobial agent can be microencapsulated so that it can be released into the wound in a time-release manner, thus providing long term treatment.

The microneedles can be disposed in any suitable pattern on the bandage. In one embodiment, the fraction of microneedles in communication with the antimicrobial agent is disposed homogeneously on one side of the bandage, while the microneedles with no connection to the antimicrobial agent are disposed on an opposite side of the bandage.

In another embodiment, the microneedles in communication with the antimicrobial agent are disposed evenly over the entire surface area of the absorbent layer.

In a preferred embodiment, the absorbent layer is a foam or woven material, such as gauze. Upon contact with fluids from a wound, the gauze absorbs the fluid, and further acts to pull the fluid and any infectious microorganisms away from the wound.

In order to prevent the absorbent layer from sticking to a wound, there can be a non-stick layer connected to a surface of the absorbent layer. The non-stick layer can be formed of any suitable material such as silicone or other polymer. The non-stick layer is formed to be permeable so that the microneedles can penetrate the layer and fluids from the wound can pass through to the absorbent layer. The non-stick layer can be formed a screen or a perforated sheet.

In a further embodiment, instead of or in addition to the microneedles, a permeable membrane is provided, which is connected to a power source, such as a battery. The battery is connected to a plurality of nano-sized light emitting diodes (LEDs) which emit UV light. The LEDs are located on the wound-side of the membrane, and emit UV light onto the wound. The absorbent layer is impregnated with a fluid such as water, that can also contain an antimicrobial compound. The battery is powered by the energy created by osmosis, when the less highly saline fluid from the absorbent layer flows through the permeable membrane to the more saline wound. The electrical energy from the osmosis is transferred to a battery where it is stored and then connected to the LEDs, which emit UV light onto the wound, to disinfect the wound. A solar panel can be added on top of the bandage to add additional power to the battery, to supplement the osmosis

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 6 shows a modification of the bandage of FIG. 5; and

FIG. 7 shows another alternative embodiment having a combination of the features of the embodiments of FIGS. 1 and 5.

DETAILED DESCRIPTION OF THE PREFERRED EMBODIMENTS

Figure 1:
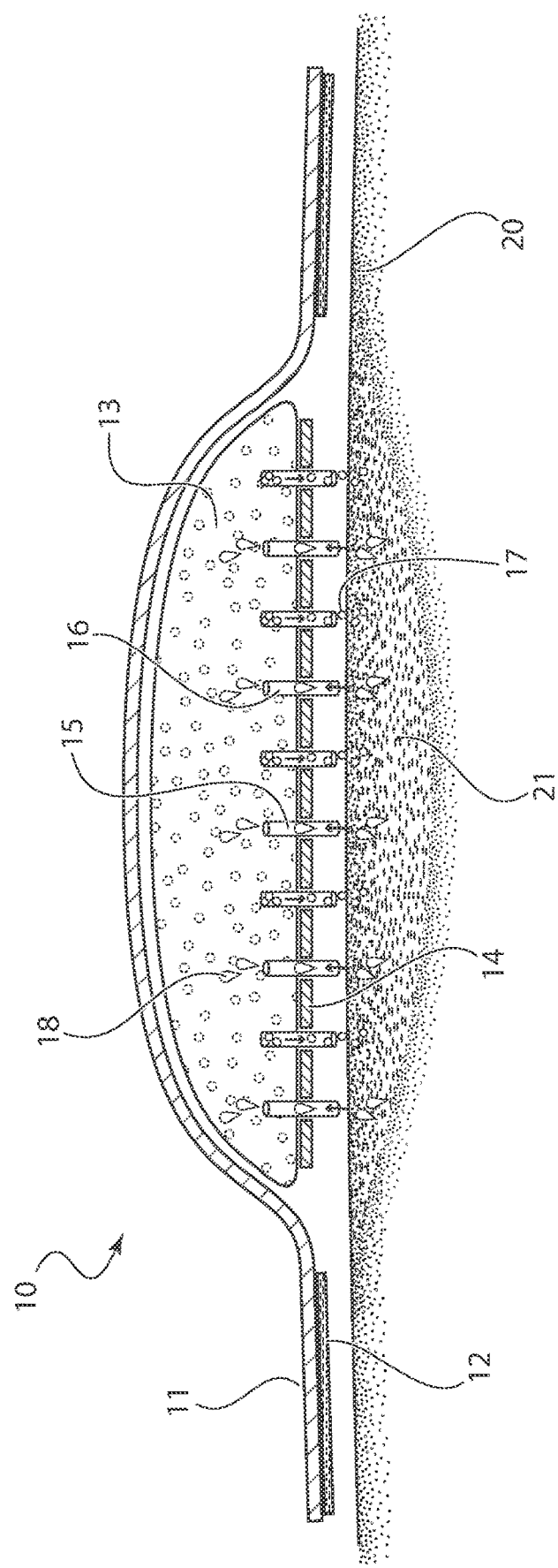
FIG. 1 shows a cross-sectional view of the bandage according to the invention prior to use.

Referring now in detail to the drawings, FIG. 1 shows a cross-sectional view of the bandage 10 according to the invention after application to a patient's skin 20 for covering a wound 21. Bandage 10 comprises a film layer 11, an adhesive layer 12 extending the length of film layer 11, and an absorbent layer 13 disposed centrally along film layer 11, so that end sections 17 of film layer 11 extend beyond absorbent layer 13. A non-stick layer 14 is applied to the bottom of absorbent layer 13 to prevent absorbent layer 13 from sticking to the wound 21. Non-stick layer 14 is water permeable and can be configured as a screen or with perforations to allow fluid to pass through to absorbent layer 13. Non-stick layer 14 can be configured of any suitable material, such as silicone or polypropylene. Film layer 11 can be manufactured from any suitable film material that is commonly used in disposable bandages. Common film materials are extruded polymers, but woven materials could also be used instead of a film.

Embedded within absorbent layer 13 is a microencapsulated antimicrobial agent 17. The antimicrobial agent 17 is configured to be released from microencapsulation upon contact with fluid, so that the agent can mix with the fluid and kill any microorganisms in the fluid. Absorbent layer 13 can be formed of any suitable material, such as foam or gauze.

Antimicrobial agent 17 can be any suitable agent, such as a topical antibiotic (erythromycin, sulfacetamide sodium, bacitracin, neomycin) or antiseptic (sodium hypochlorite, ethanol, iodine, chlorhexidine). By pulling the fluid out of the wound, bandage 10 prevents infection in the wound and speeds healing.

A plurality of microneedles 15, 16, are disposed in the bandage 10, extending between the absorbent layer 13 and the wound 21. Needles 15 act to absorb fluid 18 from wound 21 and store it in absorbent layer 13. Needles 16 are filled with microencapsulated antimicrobial agent 17, which is released through needles 16 and travels into wound 21 to speed healing. The combined action of needles 15, 16 acts to decrease inflammation and infection, while keeping the wound dry. The needles 15, 16, act as conduits both into and out of the wound 21, so that over time, fluid collecting in the wound area is continually suctioned away and treated, thus decreasing healing time and risk of infection. The needles 15 that absorb the fluid from the wound 21 are attached directly to the absorbent material, and capillary action forces the fluid 18 from the wound 21 up the needles 15, where it is absorbed by the absorbent layer 13. At the same time, the same capillary action that pulls the fluid out of the wound forces the antimicrobial agent 17, which is in liquid form, down the needles 16 and into the wound.

In addition, due to the principle of chemotaxis, any organisms affected by the antimicrobial agent 17 will be driven up the microneedles 15 to the absorbent layer 21, in order to avoid contact with the antimicrobial agent 17.

Figure 2:
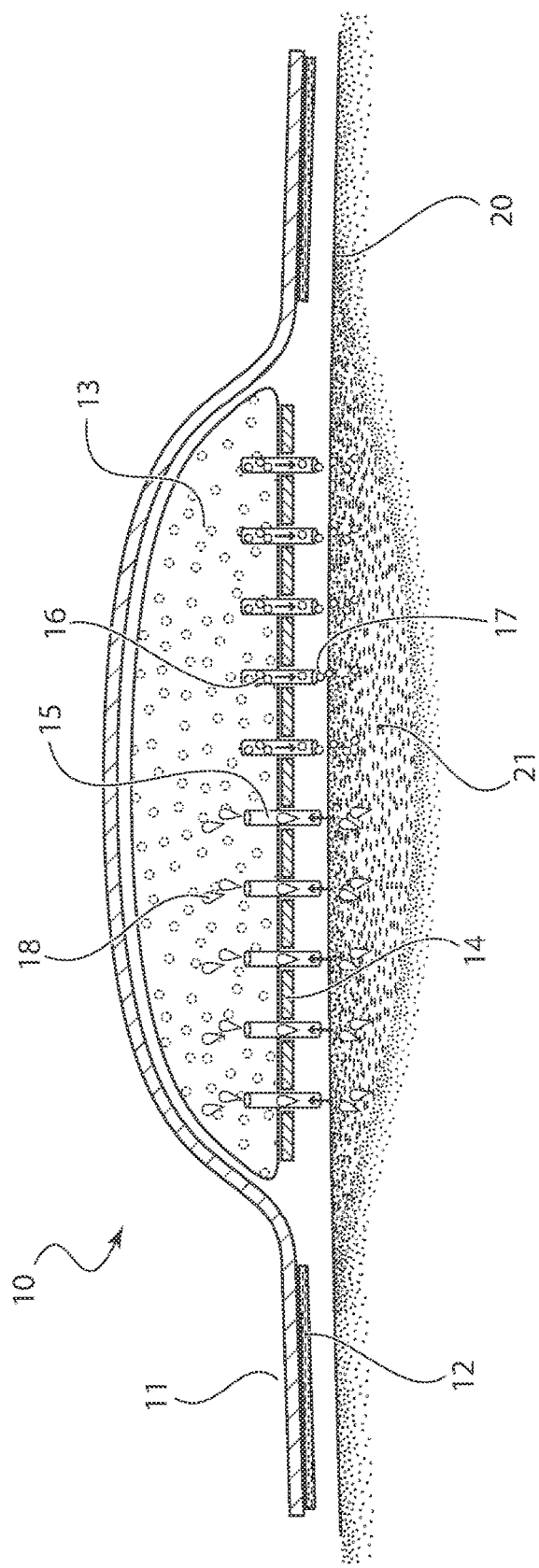
FIG. 2 shows another embodiment of the bandage.

As shown in FIG. 1, the needles 15, 16 are disposed uniformly throughout the bandage, so that the suction of wound fluid and the dispensing of the antimicrobial agent takes place evenly throughout the area. However, other arrangements could also be used, such as the one in FIG. 2, where all needles 15 are on one side of the bandage 10, and all needles 16 are on the other side, so that suction of the fluid 18 occurs on one side and dispensing of the antimicrobial agent 17 occurs on the other side.

Figure 3:
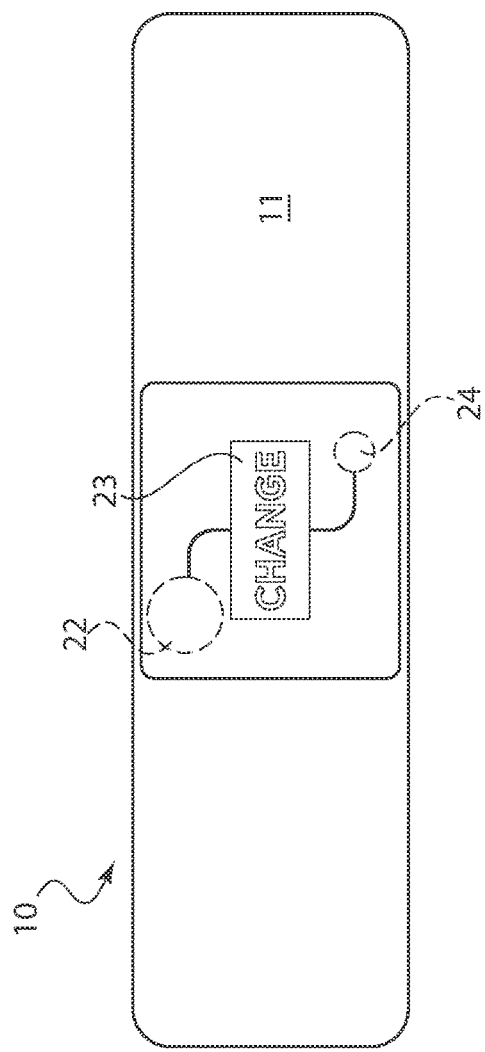
FIG. 3 shows a top view of the bandage.

As shown in FIG. 3, there can be a layer of electronic ink 23 disposed on the film layer 11, a battery 22 connected to the electronic film layer, and a moisture sensor 24 connected to the electronic film layer and the absorbent layer, wherein the electronic film layer 23 displays a message when the moisture sensor 24 senses a predetermined level of moisture in the absorbent layer 13, thus indicating time to change the bandage.

Figure 4:
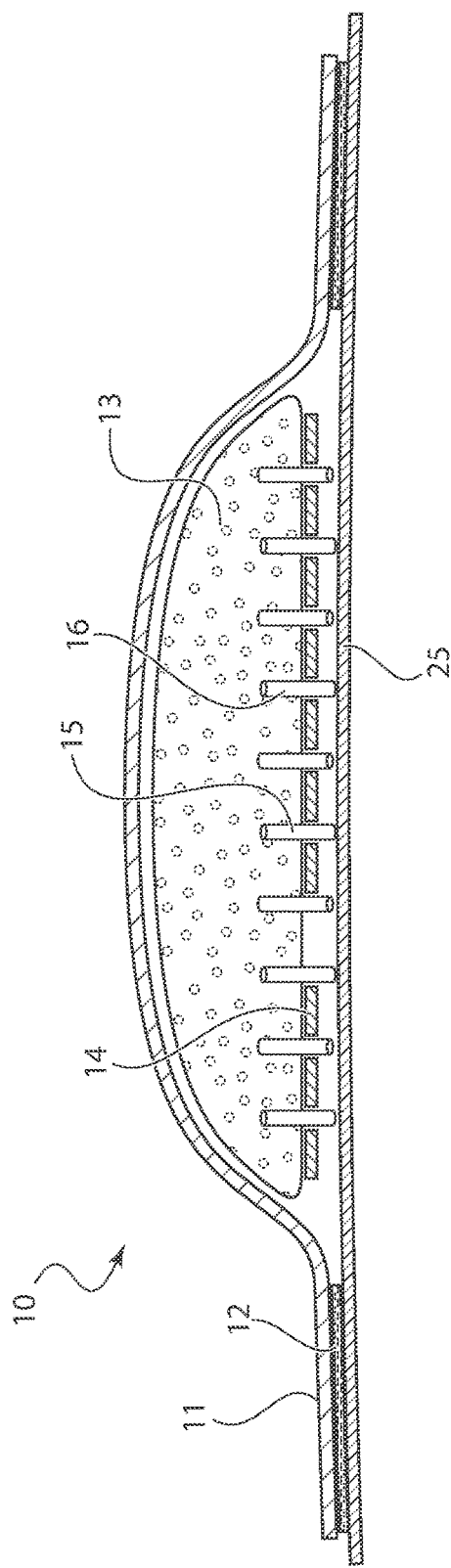
FIG. 4 shows the bandage prior to use.

As shown in FIG. 4, a release layer 25 can be placed on the bottom of the bandage to protect adhesive layer 12 as well as prevent antimicrobial agent 17 from leaking out of needles 16 prior to use.

Figure 5:
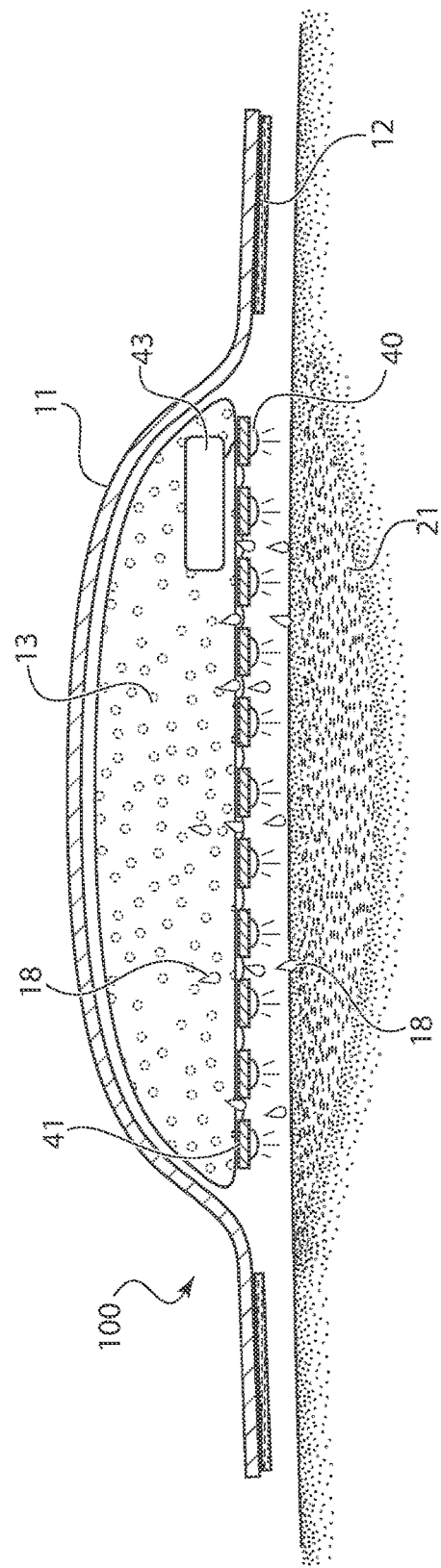
FIG. 5 shows an alternative embodiment of the bandage according to the invention.

An alternative embodiment of the invention is shown in FIGS. 5-6. Here, bandage 100, similar to bandage 10, has a film layer 11, an adhesive layer 12 extending the length of film layer 11, and an absorbent layer 13 disposed centrally along film layer 11, so that end sections 17 of film layer 11 extend beyond absorbent layer 13. Absorbent layer 13 is impregnated with a fluid such as water. Absorbent layer 13 can be a foam, a fabric, a gel or any other layer that can hold a fluid.

A permeable membrane 41 is disposed along the bottom surface of absorbent layer 13, facing wound 21. A plurality of light emitting diodes (LEDs) 40 are arranged along membrane 41, in any suitable pattern: The LEDs 40 could cover the entire wound-facing surface, or only a portion of the surface, and can be arranged with any desired density. One example is shown in FIG. 7, where the LEDs are arranged evenly spaced over the entire membrane 41.

LEDs 40 are connected to each other and to a power storage unit 43, which is also connected to membrane 41. Power storage unit 43 is charged by the electric current generated by osmosis when fluid 18 from wound 21 travels through membrane 41, as shown in FIG. 5. As the less saline fluid 18 from absorbent layer 13 flows through membrane 41 toward the more saline environment of wound 21, an electrical charge is created across the membrane. This charge is stored in power storage unit 43 and used to power LEDs 40. LEDs 40 emit light 48 in the ultraviolet spectrum, which can be effective in disinfecting wound 21 while bandage 100 is covering it. The fluid flowing from absorbent layer 13 into wound 21 could also have disinfecting properties and can be any suitable disinfectant, as long as it passes through membrane 41 to create the current required for power storage unit 43.

To supplement power storage unit 43, a photovoltaic cell 43 can be placed on bandage 100 and connected to power storage unit 43 by a wire 45, as shown in FIG. 6. Solar energy 49 can be absorbed by photovoltaic cell 43, which converts it into electrical energy for storage by power storage unit 43. Power storage unit 43 can also be charged by any other suitable method, or can come pre-charged.

The device shown in FIGS. 5-7 can be combined with the microneedle configurations of FIGS. 1-4, so that a combination of microneedles and LEDs are present in each bandage. The microneedles 15, 16 can be interspersed with the LEDs to provide the antimicrobial agent in addition to the UV light to disinfect the wound, as shown in FIG. 7.

Accordingly, while only a few embodiments of the present invention have been shown and described, it is obvious that many changes and modifications may be made thereunto without departing from the spirit and scope of the invention.

What is claimed is:
1. A bandage comprising:
a film layer having a top surface and a bottom surface;
an adhesive applied to the bottom surface; and
an absorbent layer connected to the bottom surface, the absorbent layer being impregnated with a fluid,
a permeable membrane connected to the absorbent layer;
a power storage device connected to the permeable membrane; and
a plurality of light-emitting diodes connected to the power storage device and configured to emit light in the ultraviolet spectrum;
wherein the power storage device is configured to store electricity generated by osmosis of the fluid from the absorbent layer into a wound when the bandage is applied to the wound, and wherein the power storage device is configured to supply the electrical power to the light-emitting diodes such that the light-emitting diodes emit ultraviolet light onto the wound when the bandage is applied to the wound.

2. The bandage according to claim 1, further comprising a photovoltaic cell arranged on the top surface of the film layer and being electrically connected to the power storage device, wherein the photovoltaic cell is configured to convert solar energy to electric power and supply the electrical power to the power storage device to supplement the electrical power generated by the osmosis of the fluid from the absorbent layer into the wound.

3. The bandage according to claim 1, further comprising a plurality of microneedles disposed within the absorbent layer, each one of the plurality of microneedles having an end that extends through the absorbent layer and the permeable membrane and is configured to penetrate the wound when the bandage is applied over the wound;
an antimicrobial agent disposed within the bandage and in communication with said plurality of microneedles, so that upon application of the bandage to the wound, the antimicrobial agent is transported though said plurality of microneedles to the wound.

4. The bandage according to claim 3, further comprising a cover layer over the absorbent layer and ends of the microneedles, said cover layer preventing the antimicrobial agent from exiting the microneedles, and wherein removal of the cover layer allows the antimicrobial agent to flow through the fraction of microneedles and into the wound.

5. The bandage according to claim 4, wherein the antimicrobial agent is disposed inside the microneedles prior to removal of the cover layer.

6. The bandage according to claim 4, wherein the antimicrobial agent is microencapsulated.

7. The bandage according to claim 6, wherein the microencapsulation is configured so that the antimicrobial agent is released in a time-delayed manner.

8. The bandage according to claim 1, wherein the film layer extends in at least two directions beyond edges of the absorbent layer.

* * * * *